United States Patent
Zou et al.

(10) Patent No.: US 9,402,591 B2
(45) Date of Patent: Aug. 2, 2016

(54) DYNAMIC ALIGNMENT OF SPARSE PHOTON COUNTING DETECTORS

(71) Applicant: Toshiba Medical Systems Corporation, Otawara-shi (JP)

(72) Inventors: Yu Zou, Naperville, IL (US); Yuexing Zhang, Naperville, IL (US); Xiaolan Wang, Buffalo Grove, IL (US); Zhengyan Wang, Antioch, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 144 days.

(21) Appl. No.: 13/843,043

(22) Filed: Mar. 15, 2013

(65) Prior Publication Data

US 2014/0270056 A1    Sep. 18, 2014

(51) Int. Cl.
*A61B 6/03*    (2006.01)
*A61B 6/00*    (2006.01)

(52) U.S. Cl.
CPC .............. *A61B 6/4266* (2013.01); *A61B 6/032* (2013.01)

(58) Field of Classification Search
CPC .... A61B 6/4266; A61B 6/032; A61B 6/4014; G01N 2223/1016; G01N 2223/652; G01N 23/203

USPC ........................................................... 378/19
See application file for complete search history.

(56) References Cited

U.S. PATENT DOCUMENTS

| 2008/0056437 | A1* | 3/2008 | Pack et al. ........................ 378/10 |
| 2011/0026685 | A1* | 2/2011 | Zilberstein ............ G01T 1/1611 378/197 |
| 2011/0058644 | A1* | 3/2011 | Thran et al. ...................... 378/11 |

FOREIGN PATENT DOCUMENTS

JP    2013-040859    2/2013

* cited by examiner

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

An apparatus and method for controlling movement of a plurality of fixed detectors arranged in a computed tomography (CT) system that includes a rotating X-ray source. The method including obtaining a view angle of the X-ray source, determining a tilt angle for a detector of the plurality of detectors that is within a scan field-of-view of the X-ray source at the obtained view angle so that an outer face of the detector directly faces the X-ray source, and causing the detector to be moved to the determined tilt angle.

16 Claims, 9 Drawing Sheets

DYNAMIC ALIGNMENT OF SPARSE PHOTON COUNTING DETECTORS

BACKGROUND

1. Field

The present disclosure generally relates to Computed Tomography (CT) imaging. In particular, embodiments herein relate to an apparatus and method for controlling movement of detectors mounted on a ring in a CT system.

2. Background

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed.

In one of many possible geometries, the X-ray source on top of the graph shown in FIG. 1 is emitting an X-ray beam forming a fan, traversing the object. While a wide range of values can exist, typically, the distance "C" is around 100 cm, "B" is around 60 cm, and "A" is around 40 cm. The principle of tomography requires that each point of the object is traversed by a collection of rays covering at least 180 degrees. Thus, the entire X-ray generator and detector assembly will rotate around an object. Mathematical considerations show that the tomographic conditions are met when a scan of 180 degrees plus the fan angle is performed.

Conventional X-ray detectors integrate the total electrical current produced in a radiation sensor, and disregard the amplitude information from individual photon detection events. Since the charge amplitude from each event is proportional to the photon's detected energy, this acquisition provides no information about the energy of individual photons, and is thus unable to capture the energy dependence of the attenuation coefficient in the object.

On the other hand, semiconductor X-ray detectors that are capable of single photon counting and individual pulse height analysis may be used. These X-ray detectors are made possible by the availability of fast semiconductor radiation sensors materials with room temperature operation and good energy resolution, combined with application-specific integrated circuits (ASICs) suitable for multi-pixel parallel readout and fast counting.

When operating such a photon counting X-ray detector, a high bias voltage is applied across the sensor crystal such that the electron-hole pairs generated from the radiation interaction are rapidly swept toward the collecting electrodes. Each radiation interaction event results in a pulse sent to the readout electronics, which undergoes pulse height analysis and is counted.

One major advantage of such photon counting detectors is that, when combined with pulse height analysis readout, spectral information can be obtained about the x-ray beams passing through the object and then the attenuation coefficient at each energy in the object can be reconstructed. Conventional CT measures the attenuation at one average energy only, while in reality, the attenuation coefficient strongly depends on the photon energy. In contrast, with pulse height analysis, a system is able to categorize the incident X-ray photons into several energy bins based on their detected energy. This spectral information can effectively improve material discrimination and target contrast, all of which can be traded for a dose reduction to, for example, a patient.

In fourth-generation spectral CT, the photon counting detectors (PCDs) are located on a ring and fixed on the gantry. As the X-ray source rotates, a PCD will "see" the X-ray source from a different angle. In other words, the X-ray beam will irradiate the PCD surface from different angles. On different angles, the PCDs may have different count response and energy response. This angular variation may complicate the detector response function and then data domain decomposition. Additionally, this also makes the fixed PCDs susceptible to unwanted scattered radiation.

In third-generation CT, standard practice is to use an anti-scatter grid, which is placed between the patient and the detector. However, in fourth-generation CT, the angular variation of the incident beam makes use of the anti-scatter grid challenging. Some fourth-generation CT scanners (e.g., single slice scanners) use a fixed detector array just outside the incident beam to detect scattered photons. Such arrangement helps estimate scatter for subsequent correction, but does not solve the count and energy response variation problem.

BRIEF DESCRIPTION OF THE DRAWINGS

The disclosure will be better understood from reading the description which follows and from examining the accompanying figures. These figures are provided solely as non-limiting examples of the embodiments. In the drawings.

DETAILED DESCRIPTION

Figure 1:
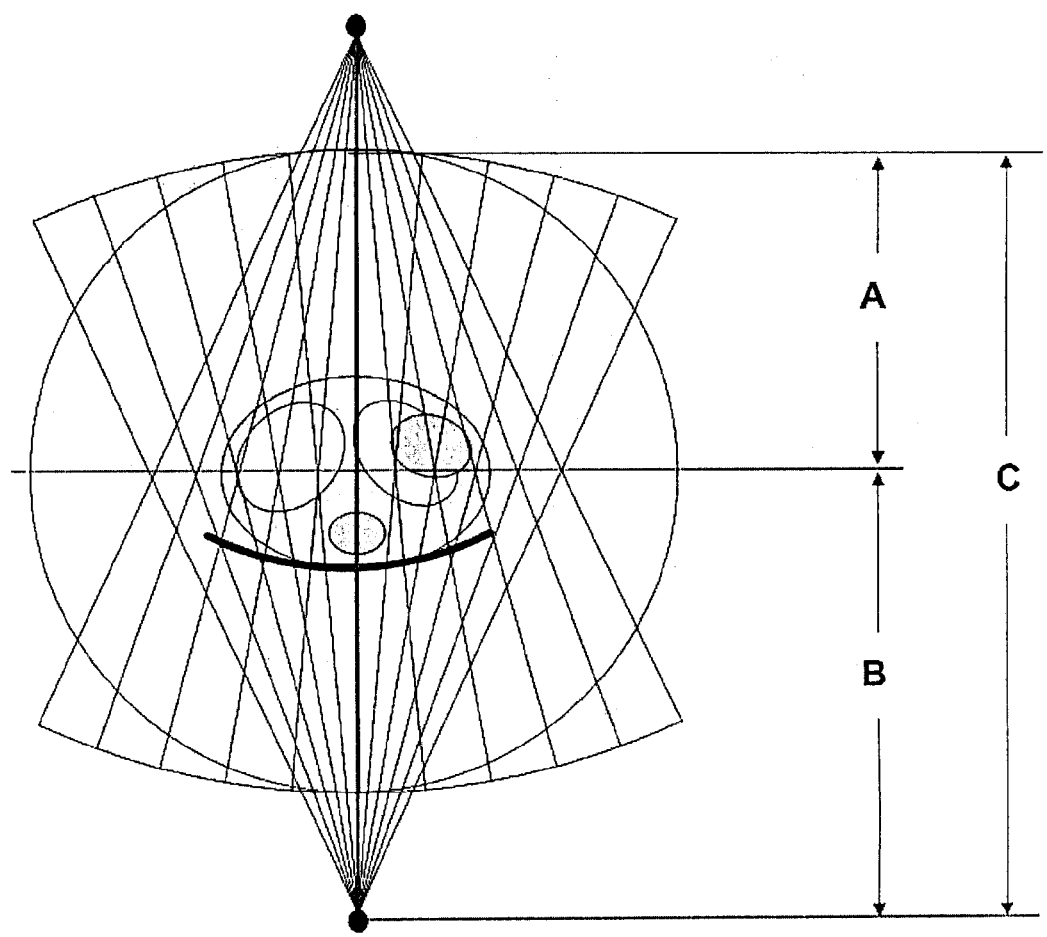
FIG. 1 illustrates an X-ray source emitting an X-ray beam forming a fan traversing an object.

In one embodiment, there is provided an apparatus for controlling movement of a plurality of fixed detectors arranged in a computed tomography (CT) system that includes a rotating X-ray source. The apparatus includes a controller configured to obtain a view angle of the X-ray source, determine a tilt angle for a detector of the plurality of detectors that is within a scan field-of-view of the X-ray source at the obtained view angle so that an outer face of the detector directly faces the X-ray source, and cause the detector to be moved to the determined tilt angle.

In one embodiment, the apparatus further includes a motor configured to move the detector to the determined tilt angle. In one embodiment, the detector is mounted on a shaft that is coupled to the motor. In other embodiment, the detector is connected to a plurality of neighboring detectors via a link, and when the motor moves the detector to the determined tilt angle, the neighboring detectors are moved in a corresponding manner.

In one embodiment, the controller is further configured to determine, for the obtained view angle, which detectors of the plurality of detectors are within the scan field-of-view, and to determine a respective tilt angle for each of the plurality of detectors within the scan field-of-view.

In one embodiment, the plurality of detectors are photon-counting detectors arranged on a ring in the CT system surrounding the X-ray source, and the controller is configured to determine the tilt angle by determining a local source angle of the X-ray source, the local source angle of the X-ray source being determined based on the view angle of the X-ray source, which is an angle between a central ray in the scan field-of-view and an x-axis at a center of the ring, and an angle between a direction the outer face of the detector is facing and the x-axis.

In one embodiment, the controller is configured to determine the local source angle of the X-ray source as $\phi(t)=\lambda s(t)-\lambda_D(k)-\pi$, where $\phi(t)$ is the local source angle of the X-ray source, $\lambda s(t)$ is the view angle of the X-ray source, and $\lambda_D(k)$ is the angle between the direction the outer face of the detector is facing and the x-axis.

In one embodiment, the controller is configured to determine the tilt angle using $\gamma(t)=\tan^{-1}((R_s \sin \phi(t))/(R_D+R_S \cos \phi(t)))$, where $\gamma(t)$ is the tilt angle, Rs is a radius of an X-ray source ring on which the X-ray source is arranged, and $R_D$ is a radius of the ring on which the plurality of detectors are arranged.

In one embodiment there is provided a method for controlling movement of a plurality of fixed detectors arranged in a computed tomography (CT) system that includes a rotating X-ray source. The method includes obtaining a view angle of the X-ray source; determining a tilt angle for a detector of the plurality of detectors that is within a scan field-of-view of the X-ray source at the obtained view angle so that an outer face of the detector directly faces the X-ray source; and causing the detector to be moved to the determined tilt angle.

In one embodiment, the method further includes moving a plurality of neighboring detectors of the detector in a corresponding manner to the detector, when moving the detector to the determined tilt angle, the detector being connected to the plurality of neighboring detectors via a link.

In one embodiment, the method further includes determining, for the obtained view angle, which detectors of the plurality of detectors are within the scan field-of-view; and determining a respective tilt angle for each of the plurality of detectors within the scan field-of-view.

In one embodiment, the plurality of detectors are photon-counting detectors arranged on a ring in the CT system surrounding the X-ray source, and the determining determines the tilt angle by determining a local source angle of the X-ray source, the local source angle of the X-ray source being determined based on the view angle of the X-ray source, which is an angle between a central ray in the scan field-of-view and an x-axis at a center of the ring, and an angle between a direction the outer face of the detector is facing and the x-axis.

In one embodiment, the determining determines the local source angle of the X-ray source as $\phi(t)=\lambda s(t)-\lambda_D(k)-\pi$, where $\phi(t)$ is the local source angle of the X-ray source, $\lambda s(t)$ is the view angle of the X-ray source, and $\lambda_D(k)$ is the angle between the direction the outer face of the detector is facing and the x-axis.

In one embodiment, the determining determines the tilt angle using $\gamma(t)=\tan^{-1}((Rs \sin \phi(t))/(R_D+R_S \cos \phi(t)))$, where $\gamma(t)$ is the tilt angle, Rs is a radius of an X-ray source ring on which the X-ray source is arranged, and $R_D$ is a radius of the ring on which the plurality of detectors are arranged.

Figure 2:
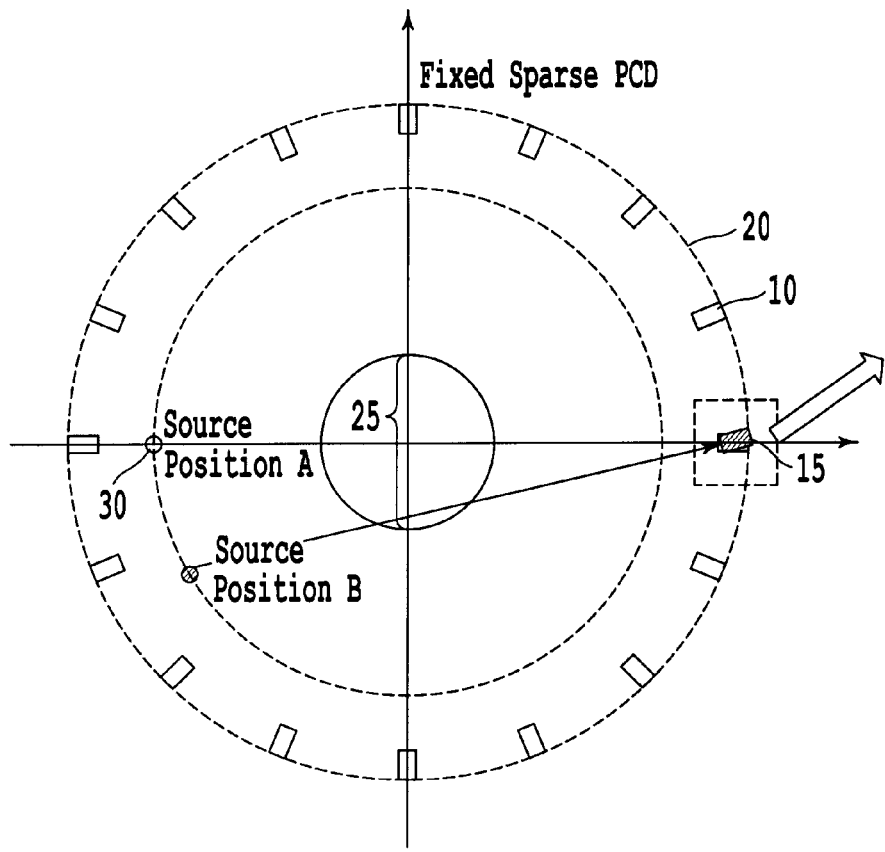
FIGS. 2 and 3 illustrate dynamic calibration of photon-counting detectors.

Turning now to the drawings, FIG. 2 shows a fourth-generation spectral CT, in which the photon-counting detectors (PCDs) 10 are located on a ring 20 and fixed on the gantry. In one embodiment, each of the PCDs 10 are 1 millimeter by 1 millimeter by 3 millimeters (1 mm×1 mm×3 mm). In one embodiment, the ring 20 may have one hundred PCDs 10. However, the ring 20 may include any other number of PCDs 10. Each of the PCDs 10 in FIG. 2 can be extended longitudinally (i.e., into the page) to form a linear array. This PCD linear array makes cone beam scan possible.

Each of the PCDs 10 are configured to be moved, rotated, or tilted around a local axis according to the position of the X-ray source 30. Thus, each PCD 10 aligns with the incident X-ray dynamically so that the PCD 10 response is independent of the X-ray source 30 position. Moreover, in one embodiment, the shadow of each PCD 10 will be minimal and not change with the position of the X-ray source 30. Moreover, in one embodiment, with an anti-scatter shield, reference from the PCDs 10 outside the field-of-view (FOV) (imaging area) 25 of the X-ray beam will be more accurate. Note that, without dynamic alignment and anti-scatter shield, the reference readings may be contaminated by scatter photons.

As illustrated in FIG. 2, when the X-ray source 30 moves from position A to position B, at least one of the PCDs 10 (in this case, PCD 15) moves/tilts around a local axis to align with or "face" the X-ray source at position B. The movement of PCD 15 in this case is illustrated by the arrows shown in FIG. 3. Note that the PCDs 10 move from "left" to "right" based on the position of the X-ray source 30.

Figure 3:
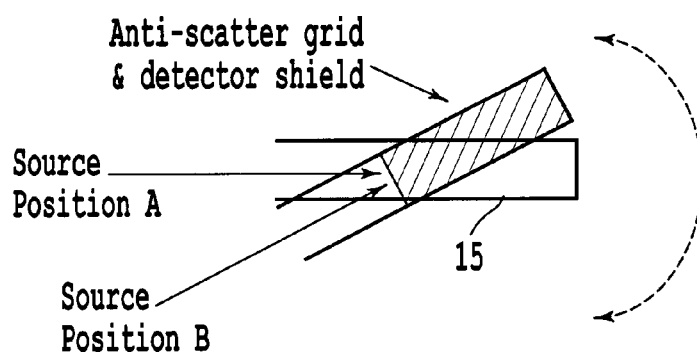

As the PCDs 10 move/rotate/tilt with respect to the X-ray source 30, the anti-scatter grid moves along with the PCDs 10, as illustrated in FIG. 3, because the anti-scatter grid is fixed to each PCD 10.

Figure 4:
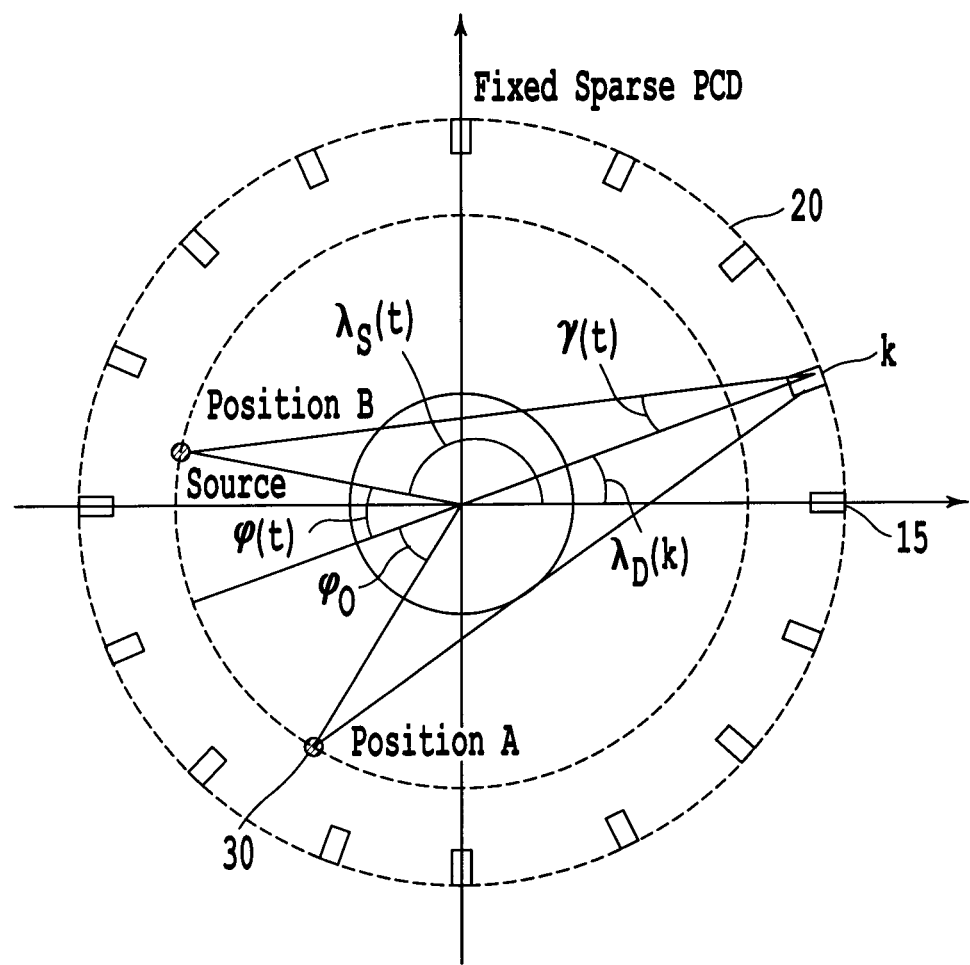
FIG. 4 illustrates the geometry of an X-ray source and photon-counting detectors.

FIG. 4 illustrates the geometry of the X-ray source 30 and the PCDs 10. In this example, the radius of the PCD ring 20 is 620 mm ($R_D$=620 mm), and the radius of the X-ray source circle is 400 mm ($R_S$=400 mm). The field-of-view (FOV) 25 of the X-ray source 30 has a diameter of 500 mm, and thus a radius of 250 mm. The rotation period of the X-ray source 30 is equal to 0.35 seconds ($\tau$=0.35 s). For a specific PCD, angle $\gamma(t)$ with $-\phi_0 \leq \phi(t) \leq \phi_0$ is the source local angle related to the line determined by the isocenter and the position of the specific PCD, where the maximum (his determined by the FOV 25. When $-\phi_0 \leq \phi(t) \leq \phi_0$, the PCD is in its duty period.

The duty angle of each of the PCDs 10 can be calculated as follows:

$$2\phi_0 = 2 \sin^{-1}(FOV/2R_S) + 2 \sin^{-1}(FOV/2R_D).$$

$$2\phi_0 = 2(38.7+23.8) = 2 \times 62.5 = 125 \text{ degrees}.$$

The duty time of each of the PCDs 10 can be calculated as follows:

$$T_{on} = (2\phi_0/2\pi)\tau = (125/360) \times 0.35 = 0.12 \text{ seconds}.$$

The off-duty time of each of the PCDs 10 can be calculated as follows:

$$T_{off} = \tau - T_{on} = 0.23 \text{ seconds}.$$

Note that during the off-duty time, the PCD 10 is outside the X-ray beam, only picking up scatter and noise.

The local angle of the X-ray source 30 can be calculated as follows:

$$\phi(t) = \gamma(t) + \sin^{-1}((R_D \sin \gamma(t))/R_S).$$

Equivalently, the detector angle $\gamma(t)$ can be related to the source local angle $\gamma(t)$ by:

$$\gamma(t)=\tan^{-1}((R_S \sin\phi(t))/(R_D+R_S \cos\phi(t))).$$

At a given time t, the source position/view angle $\lambda s(t)$ can be obtained from the rotation control module of the CT system, where $\lambda s(t)$ indicates the angle between the central ray on current view and the x-axis. For a given PCD (for example, k), at angle $\lambda_D(k)$, the source local angle can be obtained by:

$$\phi(t)=\lambda s(t)-\lambda_D(k)-\pi,$$

where $\lambda_D(k)$ indicates the angle between the central ray in the detector fan for PCD k and the x-axis. In other words, $\lambda_D(k)$ is equivalent to an angle between the direction the outer face of the PCD is facing and the x-axis. The equations above determine the detector angle $\gamma(t)$ for each of the PCDs 10 at a given time t, if the PCD is in the duty period. The duty period is determined by:

$$|\phi(t)|\le\phi_0,$$

where $\phi_0$ is the maximum of the source local angle corresponding to the FOV 25 size (in this case, the FOV 25 has a diameter of 500 mm, and thus a radius of 250 mm). Note that, although not shown in FIG. 4, angle $\lambda_D(k)$ for PCD 15 is zero when the X-ray source 30 is positioned on the x-axis directly across from PCD 15 (i.e., position A in FIG. 2).

Figure 5A:
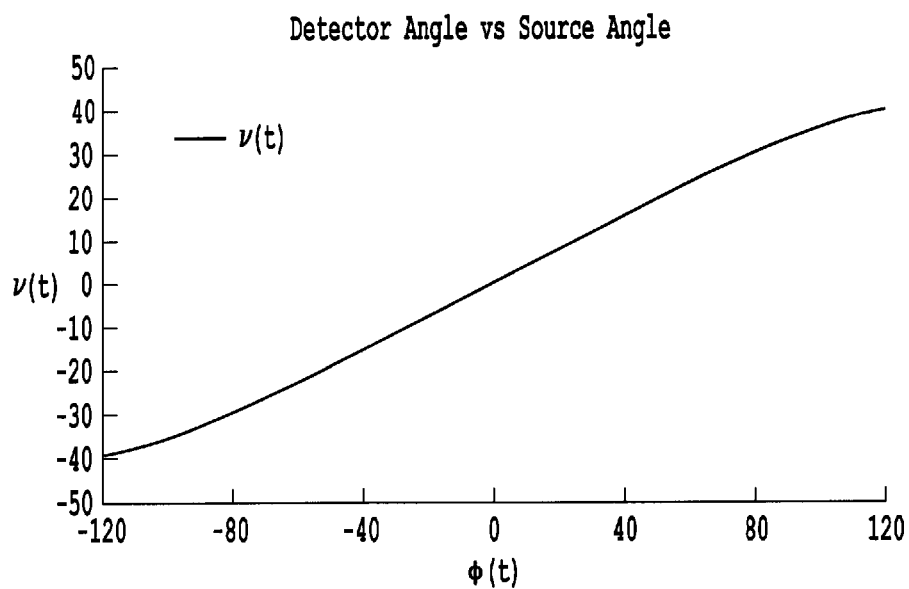
FIGS. 5A and 5B illustrate graphs of a detector angle and a source angle.
Figure 5B:
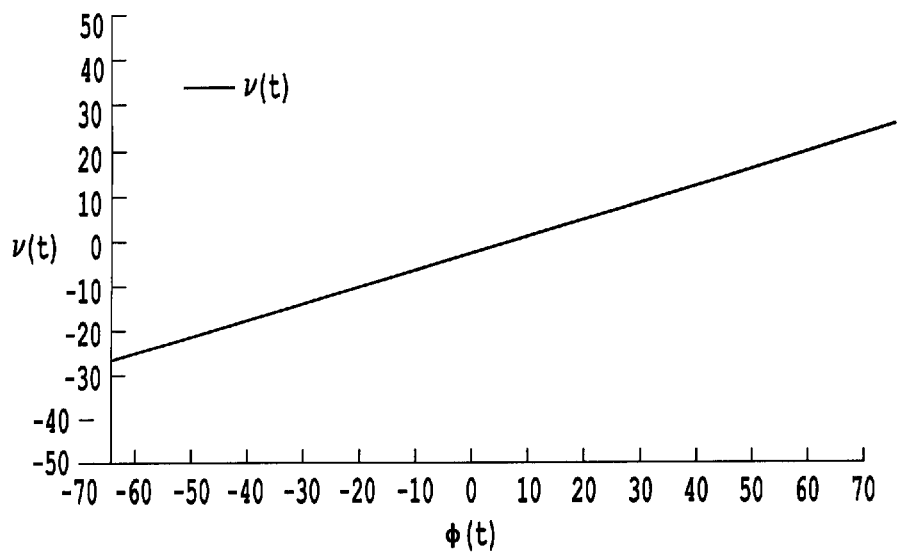

FIGS. 5A and 5B show a comparison between the PCD angle and the X-ray source angle in graph form. As can be seen from FIGS. 5A and 5B, the PCD angle is almost linear to the source angle in the duty period. This feature can be utilized in the PCD angle control. For example, one control module may control a number of PCDs.

Figure 6:
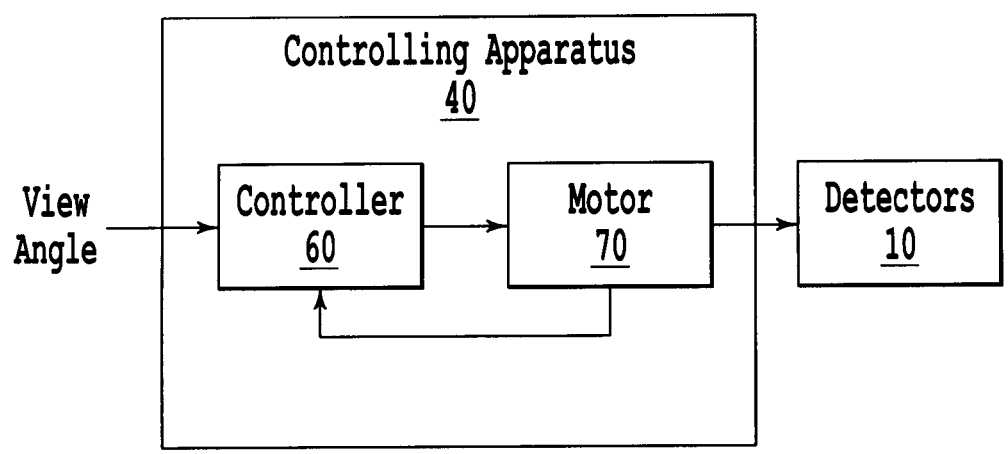
FIG. 6 illustrates a controlling apparatus.

FIG. 6 illustrates a controlling apparatus 40 for assisting in the dynamic control of the PCDs 10 by controlling the movement/tilt of the PCDs 10. Controlling apparatus 40 may be included in a CT system, or may be a stand-alone device that is configured to communicate with the CT system. Controlling apparatus 40 includes a controller 60 and a motor 70. For example, the controller 60 can be implemented by a computer processor, as discussed with reference to FIG. 10.

Figure 7:
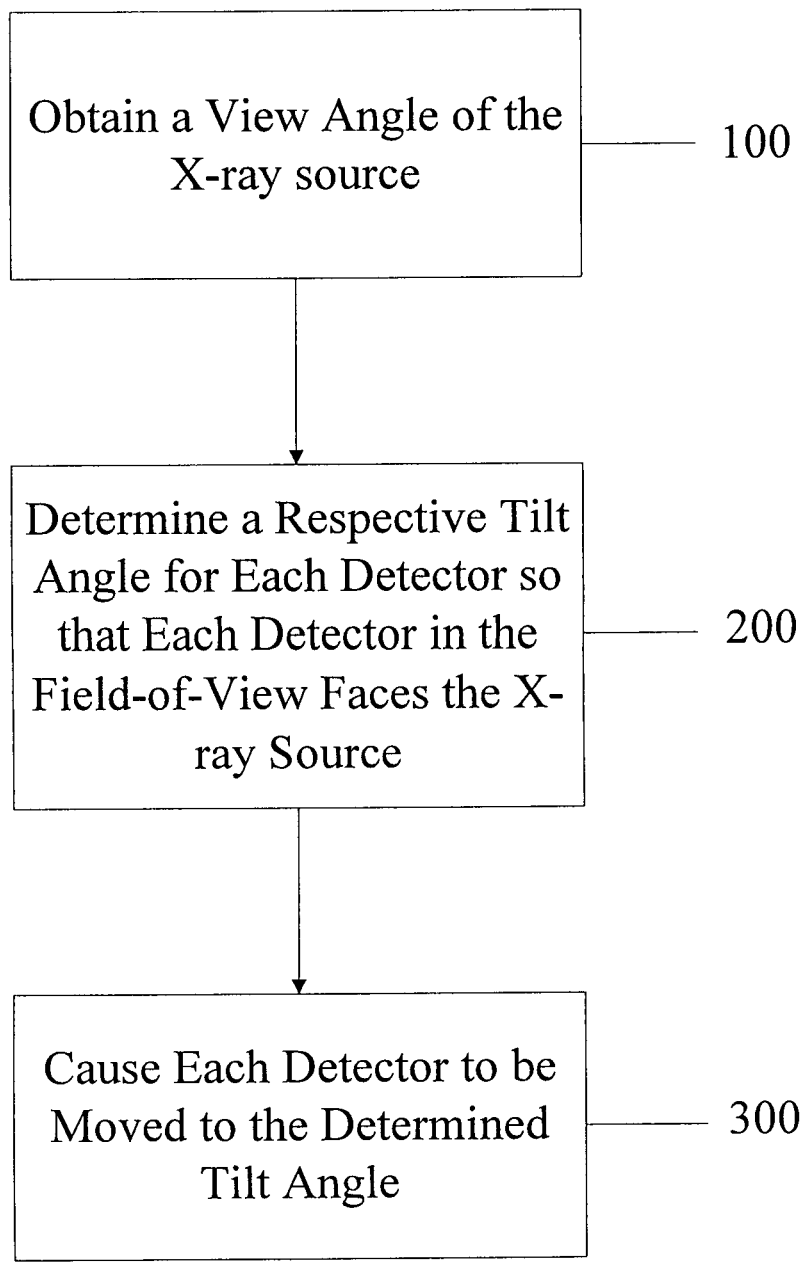
FIG. 7 illustrates a flowchart of a method of the present disclosure.

FIG. 7 is a flowchart of the process/method performed by the controlling apparatus 40. When the X-ray source 30 moves from a first position to a second position (for example, from position A to position B in FIG. 4), the controller 60 obtains a view angle of the X-ray source 30 at the second position, as shown in step 100 in FIG. 7. As noted above, the view angle may be obtained from the rotation control module of the CT system.

Next, the controller 60 determines a tilt angle for each PCD (for example, PCD k in FIG. 4) that is within the scan field-of-view of the X-ray source 30 at the obtained view angle, so that an outer face of each PCD directly faces the X-ray source, as shown in step 200 in FIG. 7. The tilt angle (indicated above as $\gamma(t)$) can be determined using the above-discussed equations. Note that not all of the PCDs 10 on the ring 20 will be in the scan field-of-view of the X-ray source 30 for a given new angle. Note that, in one embodiment, the controller 60 determines which of the PCDs 10 are within the scan field-of-view of the X-ray source 30 based on the view angle itself and the corresponding locations of the PCDs 10 on the ring 20, using geometry. If a PCD is not within the scan field-of-view of the X-ray source 30, then a tilt angle is not determined from the particular PCD. Thus, in one embodiment, the controller 60 will only determine the corresponding tilt angles for the PCDs that are within the scan field-of-view of the X-ray source 30 at a particular given time. Further, the CT system can provide the current view angle to the controlling apparatus 40, and the controlling apparatus 40 can calculate the PCD angle and determine if the PCD is in the duty period, as discussed above.

Next, once the controller 60 has determined the tilt angle, the controller 60 causes each PCD to move by controlling the motor 70 to move each PCD (for example, PCD k in FIG. 4) to the determined corresponding tilt angle, to align with the X-ray source 30 at the second position (position B in FIG. 4), as shown in step 300 in FIG. 7. Note that the motor 70 may feedback information regarding the current tilt angle of a given PCD to the controller 60, which, in turn, may use this information to control the motor 70 to further adjust the tilt angle.

The above process of the controlling apparatus 40 is performed for each PCD within the scan field-of-view of the X-ray source 30 for a given new angle, and is repeated as the X-ray source 30 moves from position to position (i.e., for different view angles). Note that, in one embodiment, each PCD that has been moved to a determined tilt angle may be moved back to its original position (at a predetermined angle corresponding to the start point of the duty period) once the PCD is not within the scan field-of-view of the X-ray source 30.

Figure 8:
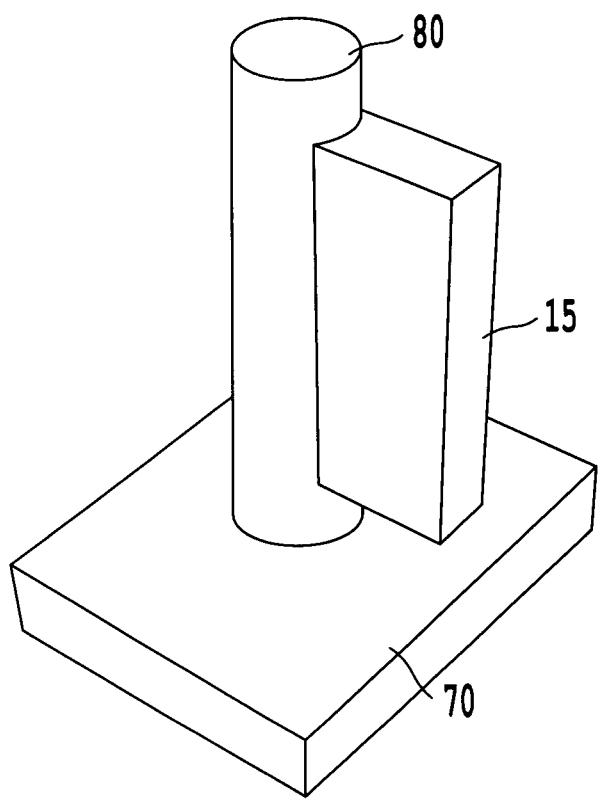
FIG. 8 illustrates an embodiment of a photon-counting detector and a swing/rotation module.

In one embodiment, a PCD (for example, PCD k or PCD 15) may be mounted on a swing/rotation shaft 80, which is mounted onto motor 70, as illustrated in FIG. 8. The motor 70 controls the movement of the swing/rotation shaft 80, which in turn controls the movement of PCD 15. Note that motor 70 may include an angle sensor.

In one embodiment, motor 70 may include a plurality of motors, each of which individually controls each of the PCDs 10. In another embodiment, motor 70 may include a plurality of motors, each of which controls a group of PCDs 10 at the same time.

Figure 9:
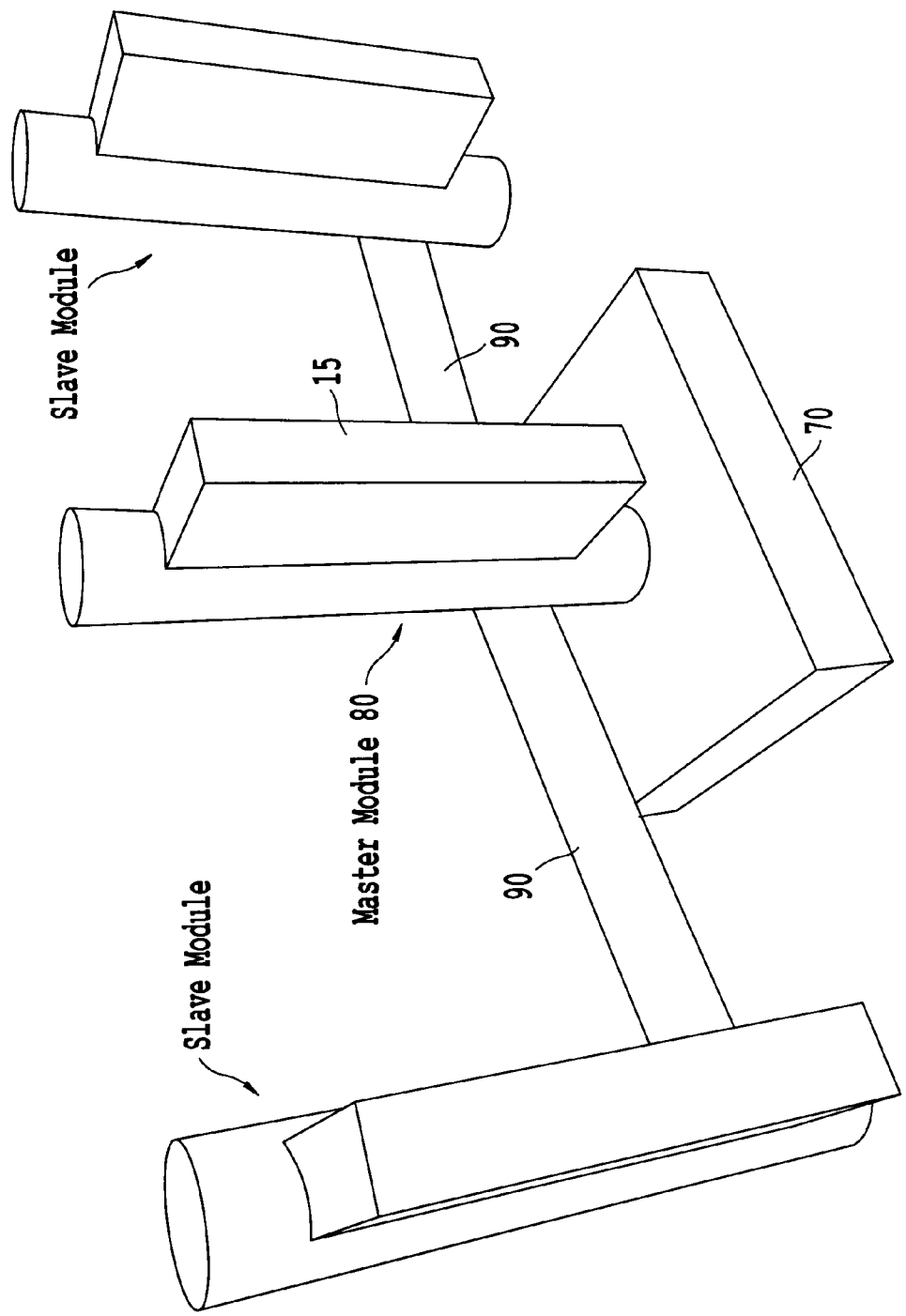
FIG. 9 illustrates a group of photon-counting detectors controlled by one master unit.

For example, as illustrated in FIG. 9, motor 70 may control a master PCD (shown as PCD 15 in FIG. 9) via the swing/rotation shaft 80. As illustrated in FIG. 9, swing/rotation shaft 80 is connected to other neighboring shafts (slave modules) of neighboring PCDs via link 90. Link 90 may be one of a belt, gear, chain, or the like. Thus, as PCD 15 is moved/tilted via the swing/rotation shaft 80, the neighboring PCDs are also similarly moved via the respective shafts connected by link 90.

Note that with a Rotary Variable Differential Transformer (RVDT) or Rotary Variable Inductance Transducer (RVIT), which may be used to measure the angular displacement of PCDs 10, the rotation/swing/tilt of the PCDs 10 can be related to the X-ray source 30 rotation since both angular data are reliable. From the view angle of the x-ray source, the PCD angle can be calculated. The controller 60 can compare the calculated tilt PCD angle with the measured angle/feedback from the RVDT or RVIT to adjust the motor.

Moreover, note that in the duty cycle, the X-ray source angle and the PCD angle are almost linear. This feature can simplify the PCD angle control. Angle control can include rotation speed control. Assume the PCD angle is linear to the source local angle, namely:

$$\gamma(t)=\alpha\phi(t).$$

The tilt angle for a given PCD k can be expressed as:

$$\gamma_k(t)=\alpha\lambda_s(t)-\alpha(\lambda_D(k)+\pi).$$

The above equation shows that different PCDs move with the source with a constant speed $\alpha$ and the initial angle of each PCD should be set according to its position. Therefore, a group of PCDs can move with one motor at speed $\alpha$ in the duty period and set to different start positions in the off-duty period. The start position is dependent on the specific PCD position.

Note that theoretically, only a one dimensional (along the channel direction) anti-scatter grid is possible with the dynamic alignment. However, the anti-scatter grid in the segment direction may be used since the variation of the PCD angle is small (around +/−25 degrees). The 2D anti-scatter grid should focus on the X-ray source. As the X-ray source moves along a circular trajectory, it may move away from the focus of anti-scatter grid in the segment/cone direction, especially for large cone angle rays.

Furthermore, note that if the PCDs in the segment direction can be slightly offset, the fan rotation of a PCD can be related to its cone angle and an accurate segment anti-scatter grid is possible. Assume anti-scatter grid in the channel and segment directions are detached. The grid in the channel direction can rotate with the PCD, and the grid in the segment direction is fixed. The fixed grid in the segment direction can be curved to focus on the source ring.

Finally, note that with the anti-scatter grid, dynamic calibration will be more accurate because, with anti-scatter grid, the PCD readings in the calibration region are less contaminated by scatter.

Figure 10:
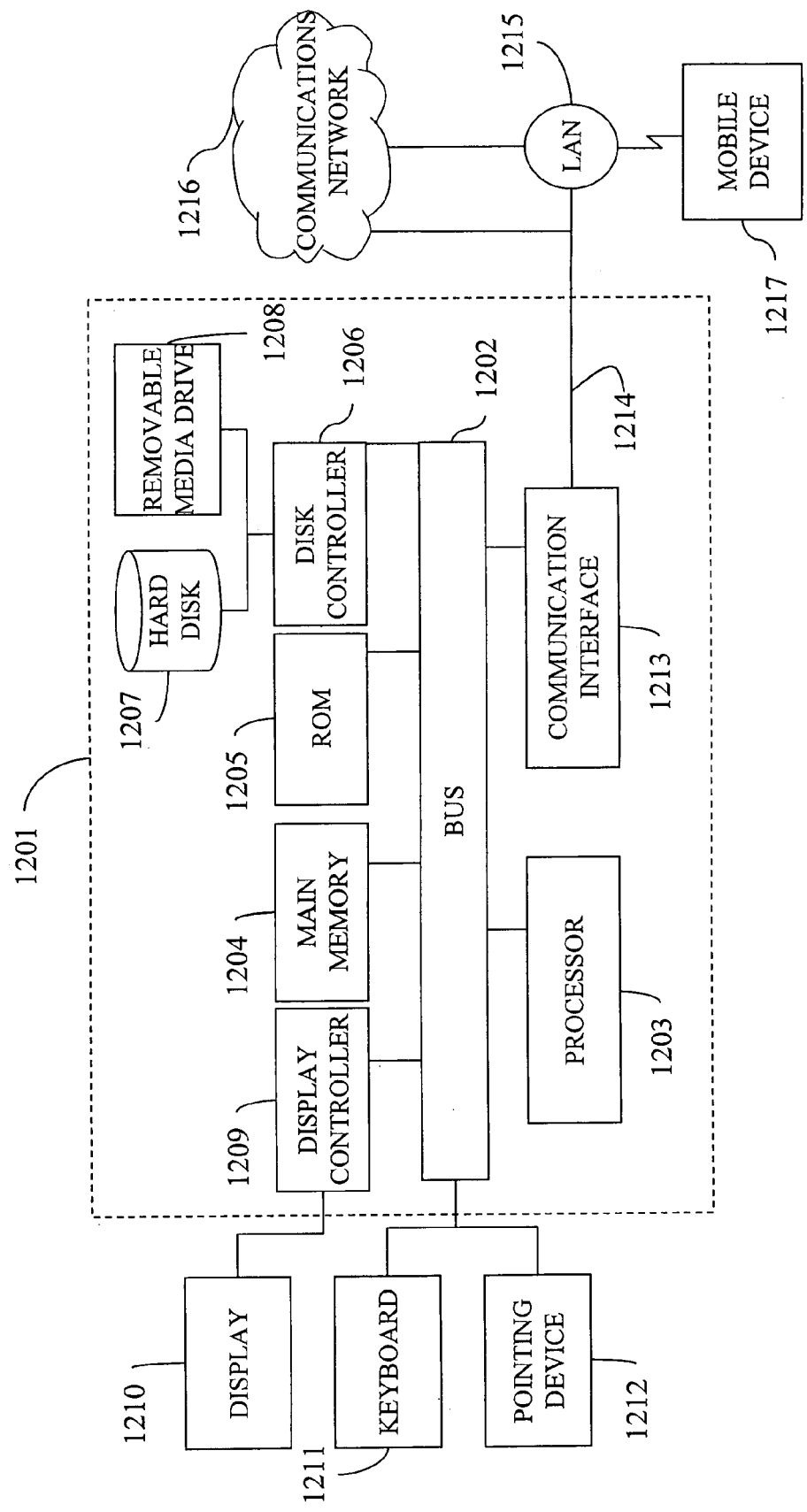
FIG. 10 illustrates a computer system that may be used to control the apparatus and upon which embodiments of the present disclosure may be implemented.

FIG. 10 illustrates a computer system 1201 that functions as, for example, the controller 60 of the controlling apparatus 40. As noted above, the controller 60, for example, may be a processor (for example, processor 1203) of computer system 1201.

The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The processor 1203 executes one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An apparatus for controlling movement of a plurality of fixed detectors arranged in a computed tomography (CT) system that includes a rotating X-ray source, the apparatus comprising:
the plurality of fixed detectors, which are arranged on a ring that is stationary with respect to the X-ray source; and
a controller configured to
obtain a view angle of the X-ray source as the X-ray source rotates about an object,
select a detector of the plurality of fixed detectors that is within a scan field-of-view of the X-ray source at the obtained view angle,
determine a tilt angle for the detector that is within the scan field-of-view of the X-ray source at the obtained view angle so that an outer face of the detector directly faces the X-ray source, and
cause the detector to be moved to the determined tilt angle in a scan plane.

2. The apparatus of claim 1, further comprising:
a motor configured to move the detector to the determined tilt angle.

3. The apparatus of claim 1, wherein the detector is mounted on a shaft that is coupled to the motor.

4. The apparatus of claim 1, wherein the detector is connected to a plurality of neighboring detectors via a link, and when the motor moves the detector to the determined tilt angle, the neighboring detectors are moved in a corresponding manner.

5. The apparatus of claim 1, wherein the controller is further configured to determine, for the obtained view angle, which detectors of the plurality of detectors are within the scan field-of-view, and to determine a respective tilt angle for each of the plurality of detectors within the scan field-of-view.

6. The apparatus of claim 1, wherein
the plurality of detectors are photon-counting detectors arranged on the ring in the CT system surrounding the X-ray source, and
the controller is configured to determine the tilt angle by determining a local source angle of the X-ray source, the local source angle of the X-ray source being determined based on the view angle of the X-ray source, which is an angle between a central ray in the scan field-of-view and an x-axis at a center of the ring, and an angle between a direction the outer face of the detector is facing and the x-axis.

7. The apparatus of claim 6, wherein
the controller is configured to determine the local source angle of the X-ray source as $$\phi(t) = \lambda_S(t) - \lambda_D(k) - \pi,$$

where $\phi(t)$ is the local source angle of the X-ray source, $\lambda_S(t)$ is the view angle of the X-ray source, and $\lambda_D(k)$ is the angle between the direction the outer face of the detector is facing and the x-axis.

8. The apparatus of claim 7, wherein
the controller is configured to determine the tilt angle using $$\gamma(t) = \tan^{-1}((R_S \sin \phi(t))/(R_D + R_S \cos \phi(t))),$$

where $\gamma(t)$ is the tilt angle, $R_S$ is a radius of an X-ray source ring on which the X-ray source is arranged, and $R_D$ is a radius of the ring on which the plurality of detectors are arranged.

9. A method for controlling movement of a plurality of fixed detectors arranged in a computed tomography (CT) system that includes a rotating X-ray source, the method comprising:
obtaining a view angle of the X-ray source as the X-ray source rotates about an object;
selecting a detector of the plurality of fixed detectors, which are arranged on a ring that is stationary with respect to the X-ray source that is within a scan field-of-view of the X-ray source at the obtained view angle;
determining a tilt angle for the detector that is within the scan field-of-view of the X-ray source at the obtained view angle so that an outer face of the detector directly faces the X-ray source; and
causing the detector to be moved to the determined tilt angle in a scan plane.

10. The method of claim 9, further comprising:
moving a plurality of neighboring detectors of the detector in a corresponding manner to the detector, when moving the detector to the determined tilt angle, the detector being connected to the plurality of neighboring detectors via a link.

11. The apparatus of claim 9, further comprising:
determining, for the obtained view angle, which detectors of the plurality of detectors are within the scan field-of-view; and
determining a respective tilt angle for each of the plurality of detectors within the scan field-of-view.

12. The method of claim 9, wherein
the plurality of detectors are photon-counting detectors arranged on a ring in the CT system surrounding the X-ray source, and
the determining determines the tilt angle by determining a local source angle of the X-ray source, the local source angle of the X-ray source being determined based on the view angle of the X-ray source, which is an angle between a central ray in the scan field-of-view and an x-axis at a center of the ring, and an angle between a direction the outer face of the detector is facing and the x-axis.

13. The method of claim 12, wherein
the determining determines the local source angle of the X-ray source as $$\phi(t)=\lambda s(t)-\lambda_D(k)-\pi,$$

where $\phi(t)$ is the local source angle of the X-ray source, $\lambda s(t)$ is the view angle of the X-ray source, and $\lambda_D(k)$ is the angle between the direction the outer face of the detector is facing and the x-axis.

14. The method of claim 13, wherein
the determining determines the tilt angle using $$\gamma(t)=\tan^{-1}((Rs\sin\phi(t))/(R_D+R_S\cos\phi(t))),$$

where $\gamma(t)$ is the tilt angle, $Rs$ is a radius of an X-ray source ring on which the X-ray source is arranged, and $R_D$ is a radius of the ring on which the plurality of detectors are arranged.

15. The apparatus of claim 1, wherein the controller determines the tilt angle based on a position of the X-ray source in the scan plane.

16. The method of claim 9, wherein the determining determines the tilt angle based on a position of the X-ray source in the scan plane.

* * * * *